(12) United States Patent
Taqi (10) Patent No.: US 12,419,763 B2
(45) Date of Patent: Sep. 23, 2025

(54) OSMOLAR DEVICES AND METHODS FOR PREVENTING TISSUE SWELLING

(71) Applicant: VASCULAR NEUROLOGY OF SOUTHERN CALIFORNIA INC., Thousand Oaks, CA (US)

(72) Inventor: Muhammad Taqi, Thousand Oaks, CA (US)

(73) Assignee: Muhammad Taqi, Thousand Oaks, CA (US)

( * ) Notice: Subject to any disclaimer, the term of this patent is extended or adjusted under 35 U.S.C. 154(b) by 0 days.

(21) Appl. No.: 18/542,256

(22) Filed: Dec. 15, 2023

(65) Prior Publication Data

US 2024/0407934 A1 Dec. 12, 2024

Related U.S. Application Data (60) Provisional application No. 63/471,738, filed on Jun. 7, 2023.

(51) Int. Cl.
*A61F 2/82* (2013.01)
*A61F 13/53* (2006.01)

(52) U.S. Cl.
CPC .... *A61F 2/82* (2013.01); *A61F 2013/530759* (2013.01); *A61F 2210/0004* (2013.01); *A61F 2210/0061* (2013.01); *A61F 2250/0059* (2013.01)

(58) Field of Classification Search
CPC ................ A61F 2/82; A61F 2210/0061; A61F 2210/0004; A61F 2250/0059; A61F 13/15; A61F 13/36; A61F 2013/530759; A61F 2013/5113; A61F 2013/51134
See application file for complete search history.

(56) References Cited

U.S. PATENT DOCUMENTS

| | | |
|---|---|---|
| 5,082,723 A | 1/1992 | Gross |
| 6,855,434 B2 | 2/2005 | Romasn-Hess |
| 7,717,871 B2 | 5/2010 | Odland |
| 8,012,116 B2 | 9/2011 | Del Bigio |
| 8,956,321 B2 | 2/2015 | Dejournett |
| 9,643,157 B2 | 5/2017 | Joshi |
| 9,682,128 B2 | 6/2017 | Tchirikov |
| 10,123,969 B2 | 11/2018 | Thorne |
| 10,420,918 B2 | 9/2019 | Rodgers |
| 11,185,574 B2 | 11/2021 | Benk |
| 11,541,005 B2 | 1/2023 | Keimel |
| 2013/0336899 A1 | 12/2013 | Li |
| 2021/0177630 A1* | 6/2021 | Epstein ............... A61F 2/844 |
| 2021/0346208 A1 | 11/2021 | Choe |
| 2021/0386919 A1 | 12/2021 | Amin |

* cited by examiner

*Primary Examiner* — Dinah Baria
(74) *Attorney, Agent, or Firm* — Ferguson Case Orr Paterson (57) ABSTRACT

Disclosed herein are devices and methods for the treatment and prevention of tissue swelling. The method involves creating an opening in a patient's skull and placement of a device in the patient's brain. The device is configured to absorb fluid from the patient's brain, thereby reducing intracranial pressure. Additionally, the device may be configured to induce an osmotic pressure to drive out fluid from the brain to reduce intracranial pressure. These methods and devices provide for a localized solution to tissue swelling and accordingly obviate the need to flood patients' vascular systems with osmolar compounds that may lead to well-documented side effects.

18 Claims, 9 Drawing Sheets

OSMOLAR DEVICES AND METHODS FOR PREVENTING TISSUE SWELLING

REFERENCE TO RELATED APPLICATIONS

This application claims the priority benefit of U.S. Provisional Patent Application No. 63/471,738, filed on Jun. 7, 2023 and entitled "OSMOLAR DEVICES AND METHODS FOR PREVENTING TISSUE SWELLING," which is fully incorporated by reference herein in its entirety.

BACKGROUND OF THE INVENTION

Field of the Disclosure

The present disclosure is related generally to improvements to devices and methods for use in the medical field for preventing or lessening tissue swelling, and in some specific embodiments, to devices such as osmolar devices capable of imbibing fluid from a patient's brain following a stroke, a traumatic brain injury, or other causes of excess fluid in the brain.

Description of the Related Art

Brain swelling, or cerebral edema, is a frequent and severe complication associated with strokes and traumatic brain injuries. The brain is encased in the skull—which is incapable of expansion—and surrounded by fluid, such as cerebrospinal fluid. In part because the skull is inelastic, there is little volume into which the brain can swell. As a result, the swelling of damaged brain tissue may increase the overall intracranial pressure and cause damage to healthy brain tissue. Accordingly, increased intracranial pressure puts patients at risk of substantial neurological degradation.

Surgical decompression such as via craniectomy may be used to treat cerebral edema; however, this technique is often a last resort due to its potential complications and side effects. Osmotherapy, the use of an osmolar agent to create an intravascular osmotic gradient that facilitates fluid extraction from the swelling/swollen brain, has become the primary method of treatment for cerebral edema. Two of the most widely used osmolar agents are Mannitol and hypertonic saline. In the treatment of cerebral edema, osmolar agents are delivered intravenously and form a new solute in the blood plasma. While the exact mechanisms by which these osmolar agents reduce intracranial pressure are not fully understood, it is clear that the use of the agents reduces the overall fluid content of both brain tissue and blood, decreasing mass and viscosity, respectively. Because osmotherapy introduces osmolar agents into the vascular system globally, it has well-documented side effects, such as hemolysis, hypotension, pulmonary edema, and electrolyte disturbances.

SUMMARY OF THE DISCLOSURE

One embodiment of a method using an osmolar device for the prevention of brain swelling according to the present disclosure comprises the steps of forming an opening in the skull of a patient adjacent to a portion of the patient's brain with excess fluid, and inserting a device comprising a solid into said opening, wherein the device is configured to absorb a portion of a fluid from said brain. The osmolar device may be configured for removable insertion in said brain.

In some embodiments, the treatment device may have an osmolarity greater than the osmolarity of said fluid. In some embodiments, the device is configured to induce an osmotic pressure upon submersion in the fluid and/or placement in brain tissue. Some devices according to the present disclosure have an osmolarity between 600-1200 mOsm/L. Upon absorption of a portion of said fluid, the device can increase in volume less than the volume of the absorbed fluid.

Another embodiment of a device for the treatment of brain swelling according to the present disclosure comprises a stent configured to be removably inserted into a blood vessel of a brain of a patient and configured with a material capable of absorbing at least a portion of a fluid from said brain. The stent may be comprised of a material having an osmolarity greater than the osmolarity of said fluid. The stent may also be comprised of a biodegradable material. In some embodiments, the stent is configured to, upon insertion into said blood vessel of said brain, induce an osmotic pressure between a tissue of said brain and said blood vessel. Some osmolar stents have an osmolarity between 600-1200 mOsm/L. Some stents according to the present disclosure are configured to expand in volume less than the volume of absorbed fluid.

These and other further features and advantages of the invention would be apparent to those skilled in the art from the following detailed description, taken together with the accompanying drawings, wherein like numerals designate corresponding parts in the figures, in which:

BRIEF DESCRIPTION OF THE DRAWINGS

The features and advantages of the various exemplary embodiments will become apparent from the following detailed description when considered in conjunction with the accompanying drawings. Where possible, the same reference numerals and characters are used to denote like features, elements, components or portions of the inventive embodiments. It is intended that changes and modifications can be made to the described exemplary embodiments without departing from the true scope and spirit of the inventive embodiments described herein as defined by the claims.

DETAILED DESCRIPTION OF THE DISCLOSURE

Embodiments incorporating features of the present disclosure include osmolar devices comprised of materials having an osmolarity greater than that of intracellular fluid of brain cells, such as neurons, astrocytes, oligodendrocytes, oligodendrocyte precursor cells, microglia, and vascular cells. The relatively high osmolarity of the osmolar devices allow for the creation of an intravascular gradient such that fluid is induced to leave brain tissue within the cranium and flow into the devices. These devices obviate or reduce the need to flood a patient's vascular system with a high osmolarity fluid, which causes undesirable side effects such as diuresis, renal and pulmonary failure, electrolyte imbalance, and rebound intracranial pressure following the withdrawal of the fluid.

In the following detailed description, numerous specific details are set forth in order to provide a more thorough understanding of embodiments incorporating features of the present disclosure. However, it will be apparent to one skilled in the art that devices, methods, and assemblies according to the present disclosure can be practiced without necessarily being limited to these specifically recited details.

Embodiments of the disclosure are described herein with reference to illustrations that are schematic illustrations of embodiments of the disclosure. As such, the actual size, components and features can be different, and variations from the shapes of the illustrations as a result, for example, of technological capabilities, manufacturing techniques and/or tolerances are expected. Embodiments of the disclosure should not be construed as limited to the particular shapes or components of the regions illustrated herein but are to include deviations in shapes/components that result, for example, from manufacturing or technological availability. The regions illustrated in the figures are schematic in nature and their shapes are not intended to illustrate the precise shape or functionality of a feature of a device and are not intended to limit the scope of the disclosure. In addition, components may be shown as one unit but may instead be a collection of components or units, or a collection of components or units may exist as one unit.

Throughout this description, the preferred embodiment and examples illustrated should be considered as exemplars, rather than as limitations on the present disclosure. As used herein, the term "disclosure," "device," "assembly," "system" "method," "present disclosure," "present device" or "present method" refers to any one of the embodiments of the disclosure described herein, and any equivalents. Furthermore, reference to various feature(s) of the "disclosure," "device," "assembly," "system," "method," "present disclosure," "present device" or "present method" throughout this document does not mean that all claimed embodiments or methods must include the referenced feature(s).

It is also understood that when an element or feature is referred to as being "on" or "adjacent" another element or feature, it can be directly on or adjacent to the other element or feature, or intervening elements or features may also be present. It is also understood that when an element is referred to as being "connected" or "coupled" to another element, it can be directly connected or coupled to the other element, or intervening elements may be present. In contrast, when an element is referred to as being "directly connected" or "directly coupled" to another element, there are no intervening elements present.

Relative terms such as "outer," "above," "lower," "below," "horizontal," "vertical" and similar terms, may be used herein to describe a relationship of one feature to another. It is understood that these terms are intended to encompass different orientations in addition to the orientation depicted in the figures.

Although the terms first, second, etc. may be used herein to describe various elements or components, these elements or components should not be limited by these terms. These terms are only used to distinguish one element or component from another element or component. Thus, a first element or component discussed below could be termed a second element or component without departing from the teachings of the present disclosure. As used herein, the term "and/or" includes any and all combinations of one or more of the associated list items.

The terminology used herein is for describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," when used herein, specify the presence of stated features, integers, steps, operations, elements, and/or components, but do not preclude the presence or addition of one or more other features, integers, steps, operations, elements, components, and/or groups thereof.

Figure 1:
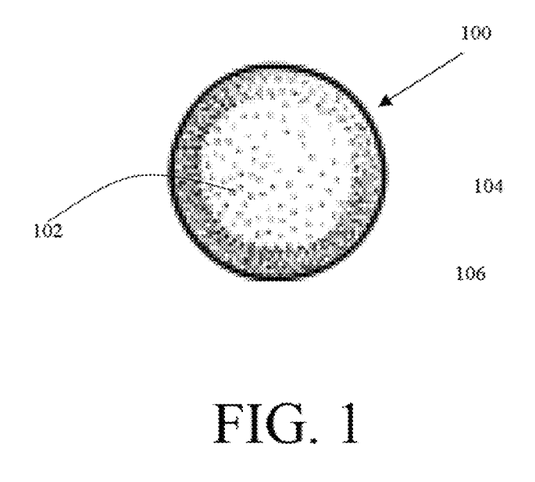
FIG. 1 shows one embodiment of an osmolar device according to the present disclosure.

FIG. 1 shows an osmolar device 100 incorporating features of the present disclosure. The embodiment depicted in FIG. 1 is generally spherically shaped, but other shapes are possible, including but limited not to cylindrical, cuboidal, spherocylindrical, complex shapes designed to maximize or minimize the ratio of surface area to volume, and other shapes as would be understood by one of skill in the art.

In some embodiments, the osmolar device 100 comprises voids 102 configured to retain fluid, such as intracellular fluid of brain cells, water, cerebrospinal fluid, and blood. Upon partial or complete submersion in a fluid, the treatment device 100 absorbs a portion or all of the fluid in which it is submerged. The voids 102 may be pores, holes, apertures, or other structures known to those of skill in the art. In some embodiments, the osmolar device 100 comprises a material with high water absorption characteristics and/or liquid absorption characteristics. In some embodiments, the treatment device 100 is configured such that the treatment device 100 expands in volume less than the volume of fluid it absorbs.

In some embodiments according to the present disclosure, the osmolar device 100 comprises a semipermeable membrane 104 capable of selective transmission of fluid. The semipermeable membrane 104 may comprise cellophane, polyvinyl alcohol, polyurethane, polytrifluorochloroethylene, other materials known in the art, or combinations thereof, though it is understood that other materials are possible. In some embodiments according to the present disclosure, the osmolar device 100 comprises solute particles 106. The solute particles 106 may be dissolved in a solution, partially dissolved in a solution, or undissolved. The solute particles may comprise sodium ions, potassium ions, chloride ions, or other solute particles known in the art, or combinations of the foregoing. The osmolar device 100 may contain a high concentration of solute particles 106, relative to, for example, the concentration of solute particles found in the intracellular fluid of brain cells, blood, or cerebrospinal fluid. It is understood that other relative concentrations are possible. Upon submersion in an environment (e.g., a fluid) having some solute concentration, the osmolar device 100, having a higher concentration of solute particles 106, generates an osmotic gradient that results in fluid crossing the semipermeable membrane and remaining within the osmolar device 100. In some embodiments according to the present disclosure, the osmolar device 100 is configured to expand in volume less than the volume of fluid it takes in. This may be accomplished, for example, by an increase in pressure within the osmolar device d 100. In some embodiments according to the present disclosure, the osmolar device 100 contains a pressure lower than atmospheric pressure at the time of placement. In some embodiments according to the present disclosure, the osmolar device 100 absorbs a volume of fluid greater than the volume of the osmolar device 100 itself, resulting in a net reduction in volume and, thus, pressure (e.g., within the cranium).

Figure 2A:
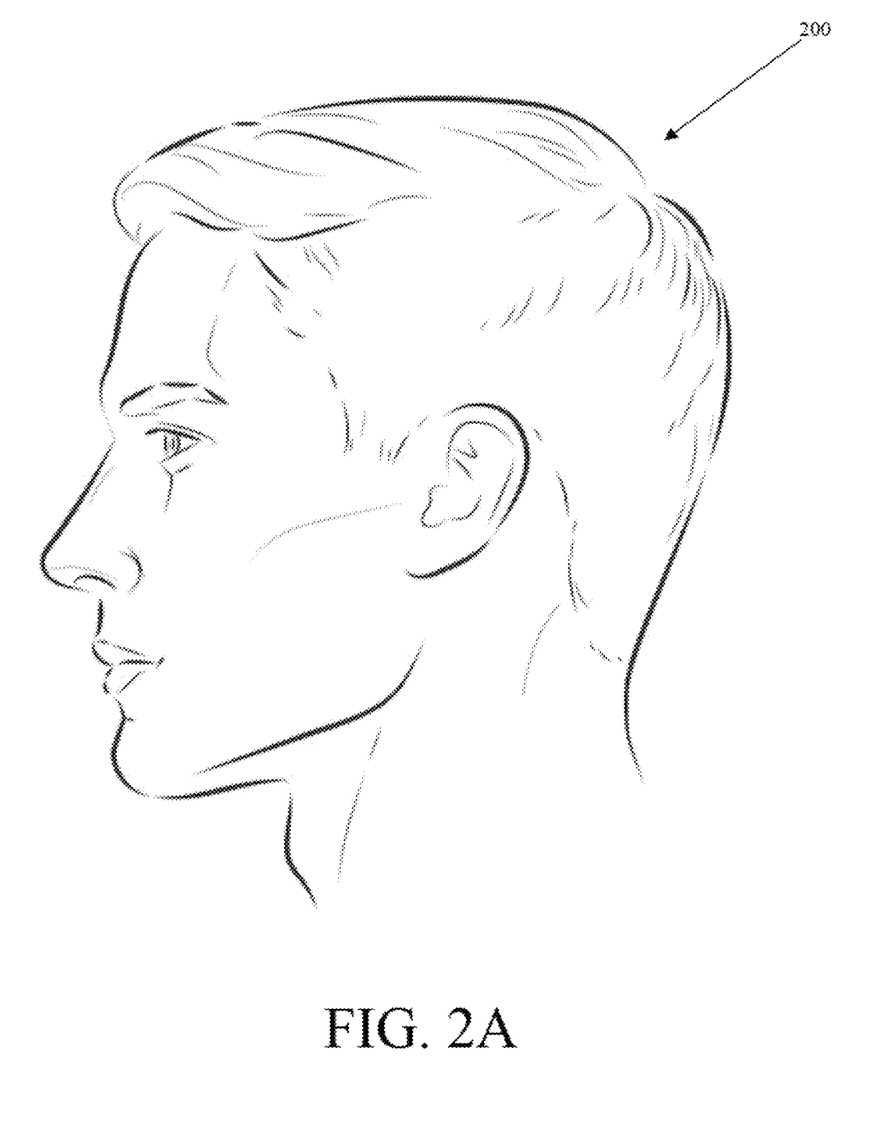
FIGS. 2A and 2B show the head of a patient undergoing treatment according to one embodiment of the present disclosure.
Figure 2B:
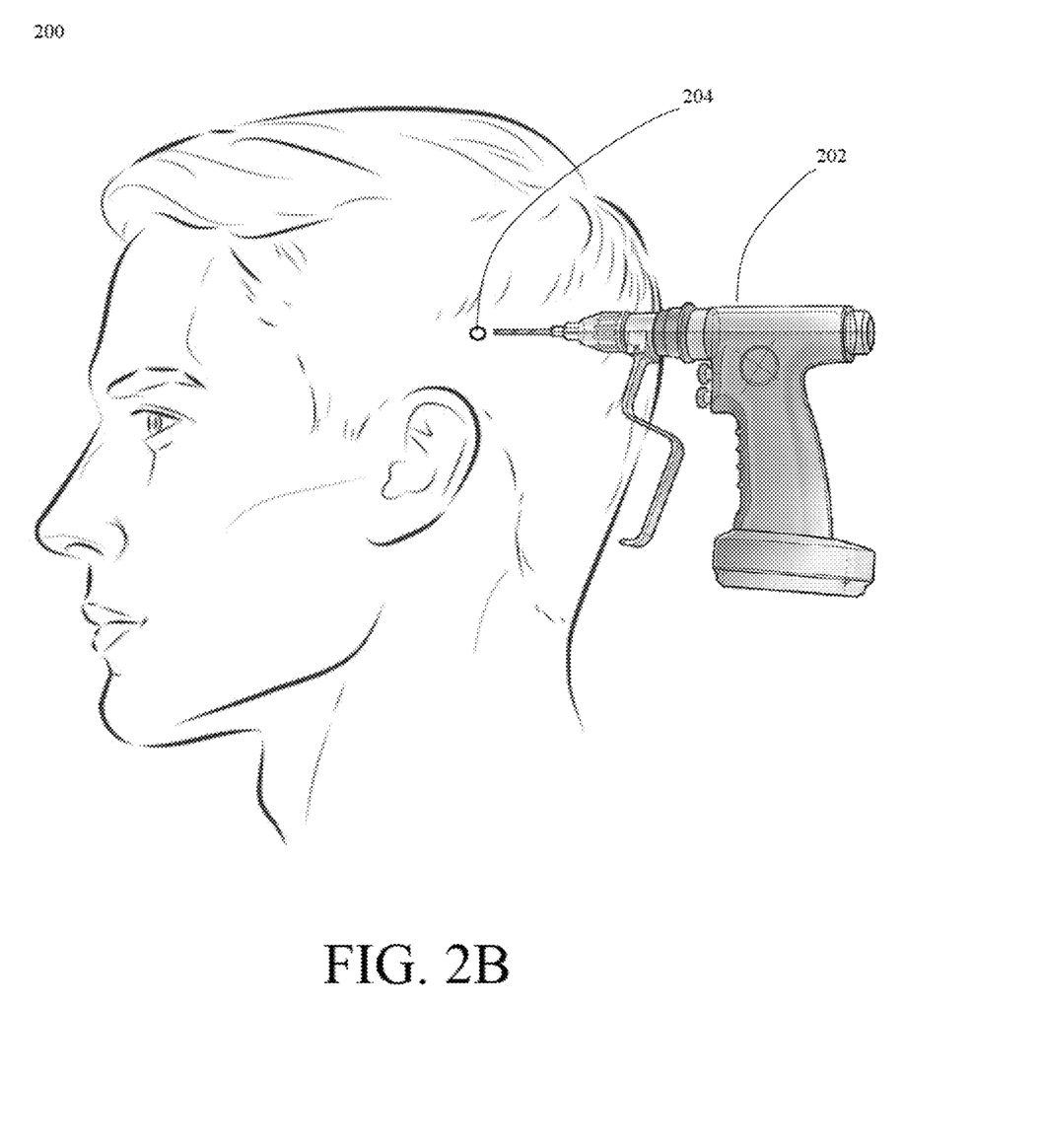

FIGS. 2A and 2B depict a patient 200 exhibiting cerebral edema. In some embodiments according to the present disclosure, a drilling device 202 is used to create a hole 204 through the skull of the patient 200 proximal to the location of the cerebral edema. In some embodiments according to the present disclosure, the drilling device 202 is configured to create a hole 204 having a diameter greater than the diameter of the osmolar device 100. In some embodiments according to the present disclosure, multiple holes are created in the skull of the patient 200, and/or multiple devices 100 can be utilized, such as through the same hole 204 and/or through a plurality of holes 204 (e.g., respective holes 204 for each device 100). Other methods of insertion are possible as would be understood by one of skill in the art.

Figure 3A:
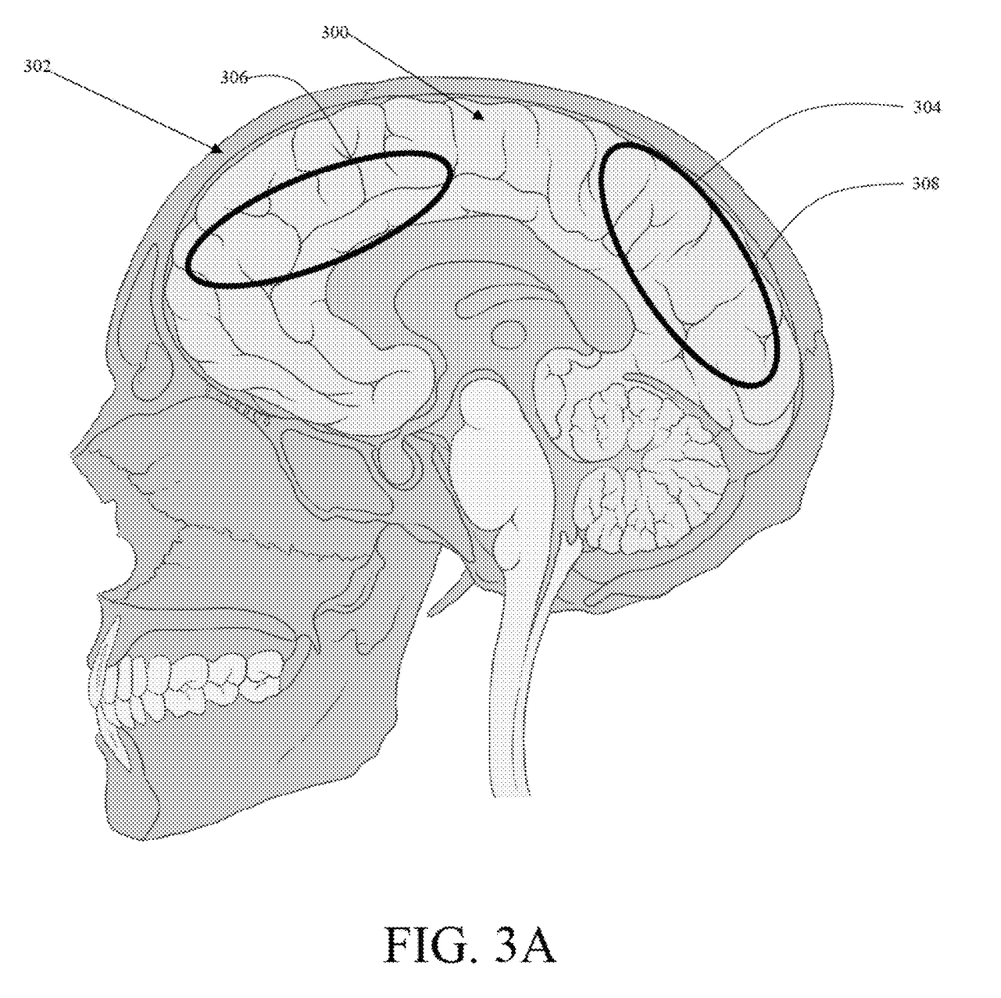
FIGS. 3A and 3B respectively show views of the skull of the patient t shown in FIGS. 2A and 2B with and without administration of the osmolar device shown in FIG. 1.
Figure 3B:
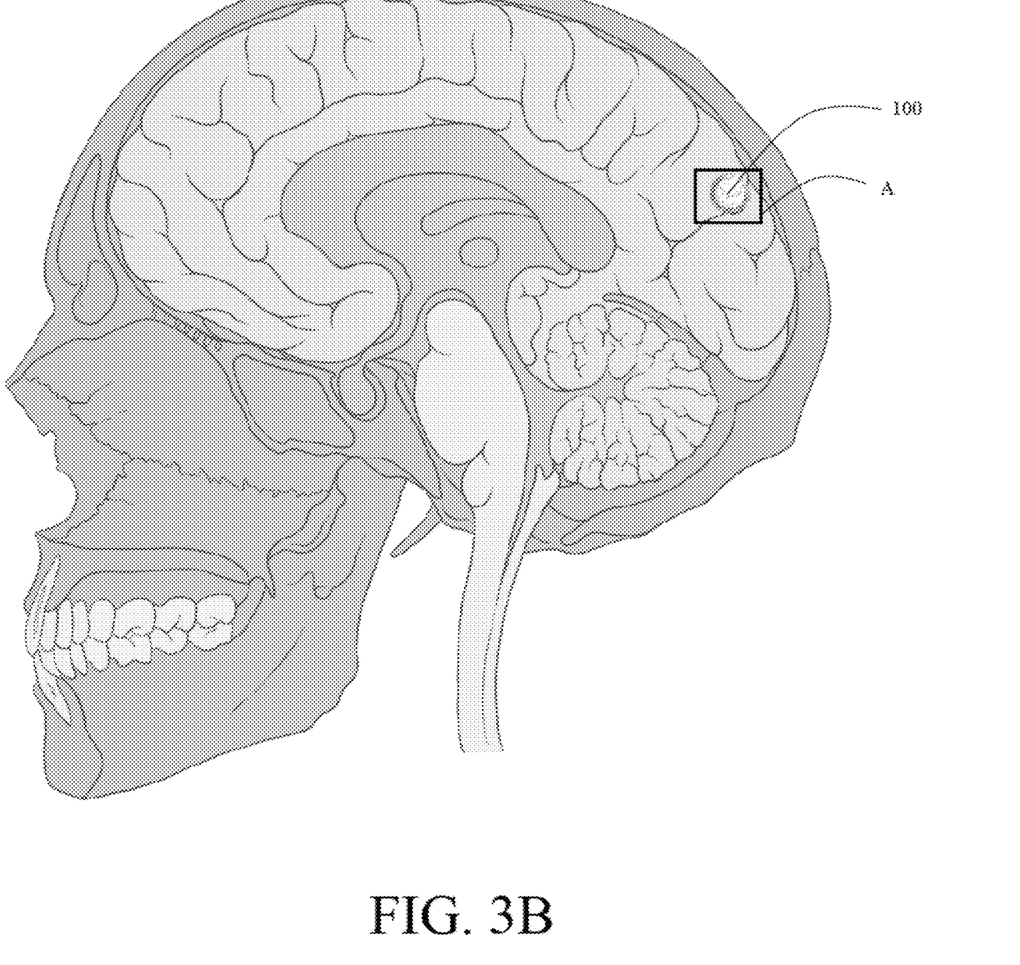

FIGS. 3A and 3B show the brain 300 in the skull 302 of the patient 100. The brain 300 comprises a damaged region 304 and a healthy region 306, with the damaged region 304 exhibiting edema. The brain 300 is surrounded by fluid 308, which may be cerebrospinal fluid. In addition to surrounding the brain 300, the fluid 308 may be located within tissue of the brain 300. For example, fluid 308 may be the intracellular fluid of brain cells, such as neurons, astrocytes, oligodendrocytes, oligodendrocyte precursor cells, microglia, and vascular cells. It is understood that damaged region 304 may exhibit edema due to stroke, traumatic brain injury, tumor, infection, or other causes known in the art, or unknown causes. In some embodiments according to the present disclosure, osmolar device 100 is inserted into the damaged region 304, which can specifically prevent or reduce expansion of the damaged region 304, thus reducing the overall brain volume that is damaged compared to expansion without the osmolar device 100. Placement of the osmolar device 100 in the damaged region 304 as opposed to other areas of the brain is also beneficial in that it avoids surgical manipulation of healthy brain tissue, which could cause complications or damage that tissue independent of the cerebral edema.

Figure 4:
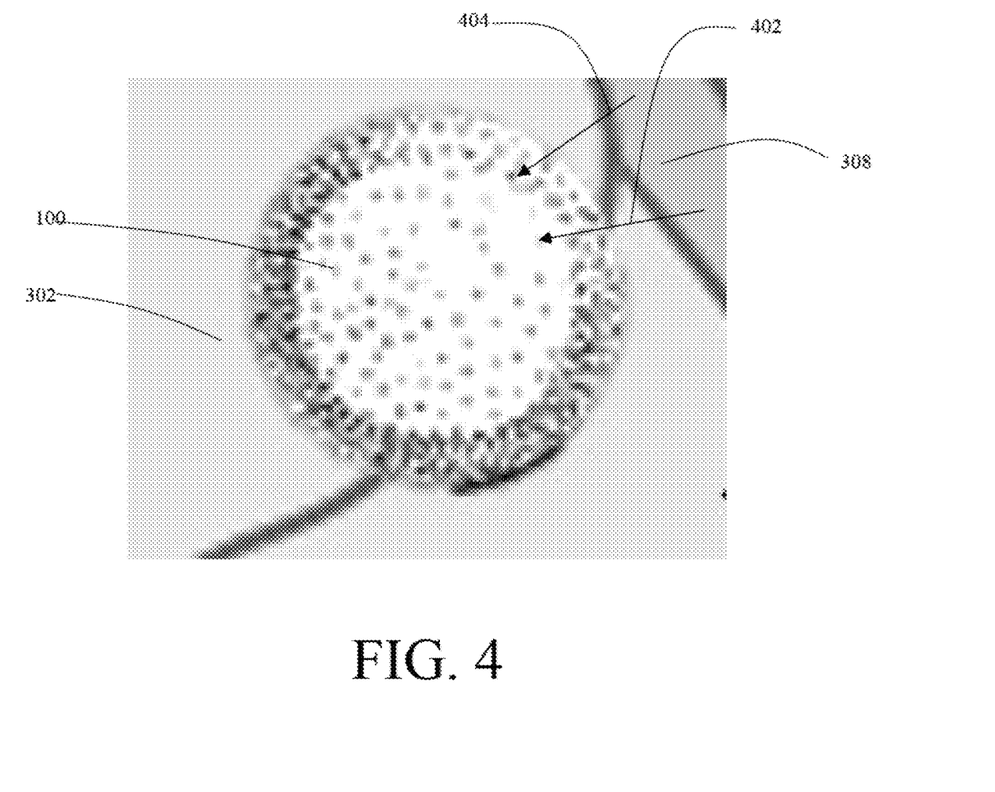
FIG. 4 shows a magnified view of area A from FIG. 3B.

FIG. 4 shows a magnified view of brain portion A shown in FIG. 3B. In some embodiments according to the present disclosure, an osmolar device 100 is inserted into the damaged region 304, proximal to the fluid 308. In some embodiments according to the present disclosure, the osmolar device 100 induces an osmotic gradient such that the fluid 308 flows into the device 100 and/or is retained within the device 100. While the fluid 308 is depicted in FIG. 3A as outside the damaged tissue 304, it is understood that fluid 308 may be contained within the damaged tissue 304 or the healthy tissue 306, such as intracellular fluid. In these embodiments, the osmolar device 100 has an osmolarity greater than that of the fluid 308. By way of example, the fluid 308 may be cerebrospinal fluid, having an osmolarity of between 290.5-291.5 mOsm/L, and the osmolar device 100 may have, for example, an osmolarity of 300 mOsm/L or greater, 450 mOsm/L or greater, 600 mOsm/L or greater, 300-1200 mOsm/L, 450-1200 mOsm/L, 600-1200 mOsm/L, or other ranges as would be understood by one of skill in the art.

Arrows 402 and 404 show a possible direction of flow of the fluid 308 into the osmolar device 100. While not pictured in FIG. 4, fluid 308 may also flow from the damaged tissue 304 into the device 100. In some embodiments according to the present disclosure, voids 102 are configured to absorb the fluid 308 by, for example, capillary action. In some embodiments of the present disclosure, the osmolar device 100 is configured to expand in volume less than the volume of fluid 308 it absorbs; and in some embodiments, the osmolar device 100 is designed such that the absorbed volume of fluid 308 is larger than the volume of the osmolar device 100 itself (including absorbed fluid). For instance, osmolar device 100 may have an internal pressure less than atmospheric pressure prior to insertion. As a result, when osmolar device 100 takes in fluid 308, the internal pressure of the device increases without a substantial increase in volume.

In some embodiments of the present disclosure, osmolar device 100 may be removed. The timing of removal may be based on, for example, the amount/volume of fluid absorbed (e.g., once a predetermined volume of fluid 308 has been absorbed by the osmolar device 100), a chosen period of time to allow for absorption, or any number of other factors or combinations thereof.

Figure 5:
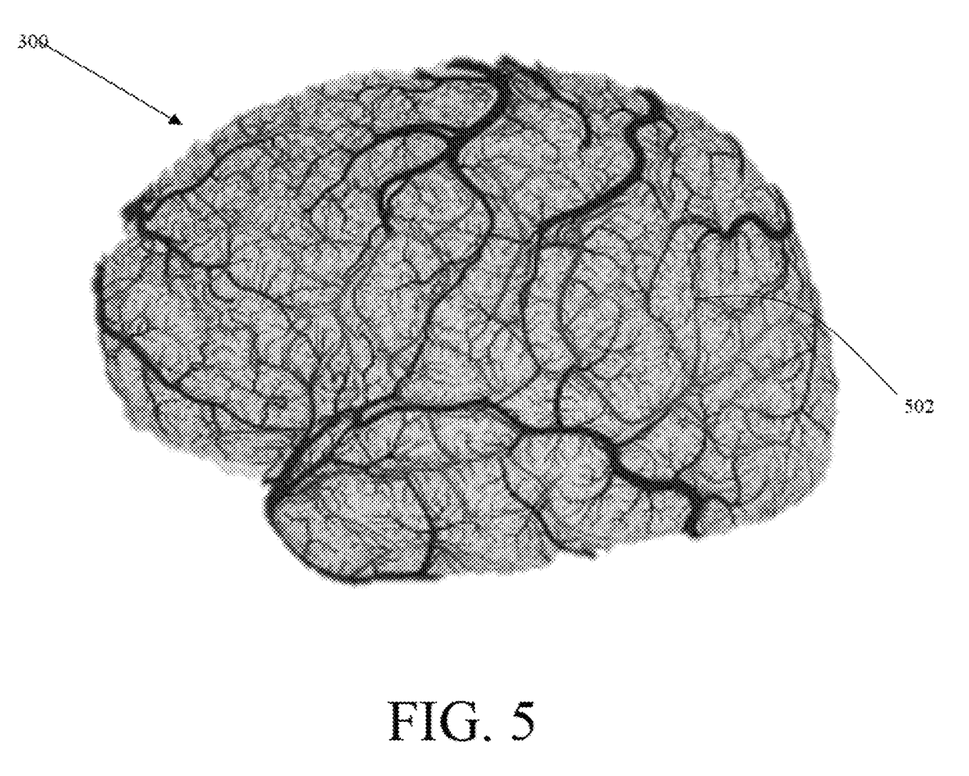
FIG. 5 shows the brain of FIG. 3A with blood vessels overlaid thereon.
Figure 6:
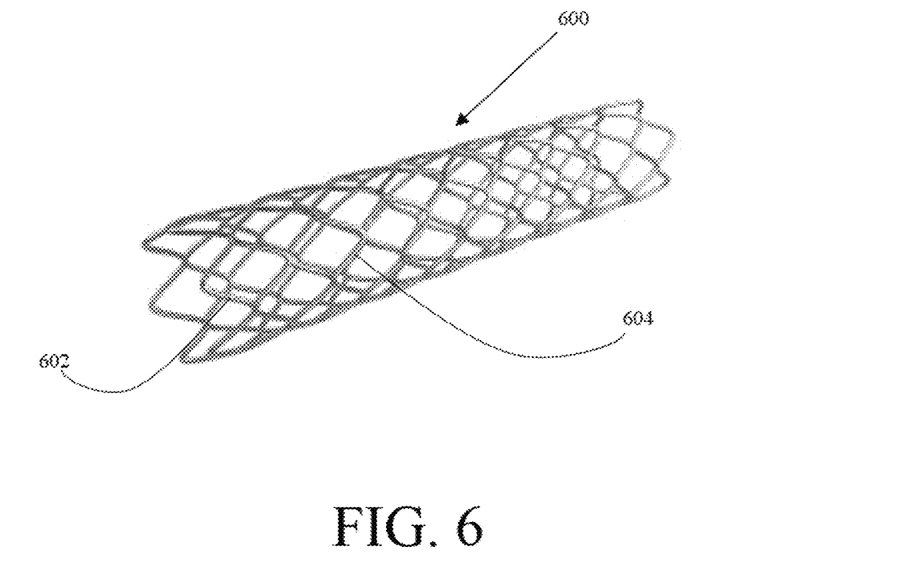
FIG. 6 shows another embodiment of an osmolar device according to the present disclosure.

FIG. 5 shows the patient's brain 300 of FIGS. 3A and 3B with visible blood vessels 502. FIG. 6 shows another embodiment of an osmolar device according to the present disclosure in the form of an osmolar stent 600. It is understood that the osmolar stent 600 may be formed in different structures and configurations, such as coil, mesh, Wall, Cypher, and other stent structures known in the art. In some embodiments according to the present disclosure, the osmolar stent 600 comprises a material with a high osmolarity. In some embodiments according to the present disclosure, the osmolar stent 600 comprises structural support segments 602 and osmolar material segments 604. The structural support segments are comprised of a material having sufficient structural integrity to maintain the shape of the osmolar stent 600. The osmolar material segments 602 comprise a material with high osmolarity. In some embodiments of the present disclosure, structural support segments 602 are also osmolar material segments. In some embodiments according to the present disclosure, the osmolar stent 600 comprises an absorbent material capable of absorbing fluid 308. In some embodiments of the present disclosure, the osmolar stent 600 comprises a base stent (e.g., a bare metal stent) with a coating of osmolar material. Many materials (e.g., metals and combinations of metals) may be used for the bare metal stent, such as 316L stainless steel, platinum, nickel, titanium, alloys, and other metals known in the art. It is understood that the osmolar stent 600 may comprise biodegradable materials, such as iron-based and magnesium-based alloys, that break down and corrode over time.

Figure 7:
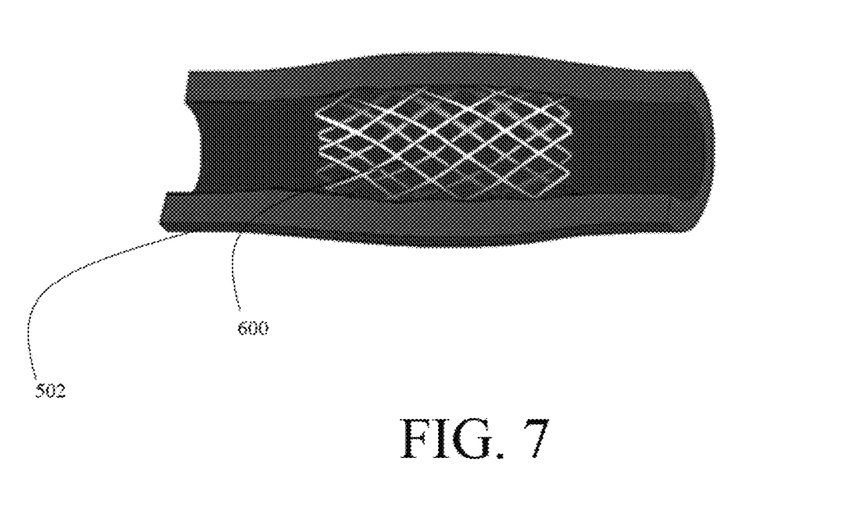
FIG. 7 shows a sectional view of the embodiment of FIG. 6 deployed in a blood vessel of FIG. 5.

FIG. 7 shows the osmolar stent 600 deployed in a blood vessel 502 of the brain 500 shown in FIG. 5. Like the osmolar device 100, in some embodiments according to the present disclosure, the osmolar stent 600 may be inserted into a blood vessel 502 via a hole 204 drilled into a patient's skull by a drilling device 202. In other embodiments according to the present disclosure, osmolar stent 600 may be delivered to a blood vessel 502 by a catheter. Other insertion methods are possible as would be understood by one of skill in the art. It is understood that osmolar stent 600 may be configured to be delivered to the blood vessel 502 in a contracted state and thereafter expanded such that the stent 600 is frictionally fixed in place within the blood vessel 502. In some embodiments according to the present disclosure, osmolar stent 600 induces an osmotic pressure such that fluid 308 flows into the blood vessel 502 from the brain tissue 300, and is carried away with blood, absorbed into the osmolar stent 600, or both.

In some methods of treating brain swelling embodying the present disclosure, the osmolar device 100 comprises a shell 108 (not pictured in FIGS. 1-7) defining one or more chambers 110 (also not pictured, and referred to in the singular throughout, although it is understood that multiple chambers 110 are possible), such as the osmotically enhanced absorbent structures disclosed in U.S. Pat. No. 5,082,723 to Gross et al., which is fully incorporated by reference herein in its entirety. Structures and/or methods from U.S. Pat. No. 6,855,434 to Romasn-Hess et al., which is fully incorporated by reference herein in its entirety, may also be utilized in embodiments of the present disclosure. In some such embodiments, the chamber 110 comprises solute particles 106. The solute particles 106 can be, in certain embodiments, solid, solutions in other embodiments, and/or gels in yet other embodiments. One of skill in the art would understand that other solute particle 106 configurations are possible.

In some embodiments of an osmolar device 100 according to the present disclosure, the shell 108 comprises an absorbent material. In even more specific embodiments, the shell 108 comprises a superabsorbent material, such as a material capable of absorbing two or more times its weight in water, five or more times its weight in water, ten or more times of its weight in water, or more. It is understood that other weight multipliers are considered in this disclosure and that the examples provided above are merely exemplary in nature. In other embodiments according to the present disclosure, the shell 108 is comprised of a nonabsorbent material or a material that is not capable of absorbing its weight in water.

In some embodiments according to the present disclosure, the volume of the chamber 110 relative to the surface area of the shell 108 is tuned to achieve a predetermined amount of fluid—such as the fluid 308—absorption upon at least partial submersion in fluid 308. For example, the ratio of chamber 110 volume to shell 108 surface area may be 1:10 or greater, 1:50 or greater, 1:100 or greater, 1:500 or greater, 1:1000 or greater, 1:10 or smaller, 1:50 or smaller, 1:100 or smaller, 1:500 or smaller, or 1:1000 or smaller. It is understood that these example ratios are not intended to limit this disclosure and that other ratios are contemplated.

The amount of osmotic material, i.e. solute particles 106, contained within the chamber 110 can be predetermined to permit a desired volume of fluid 308 to be imbibed into the chamber 110. For example, the chamber 100 can be ¼ filled or less, ½ filled or less, ¾ filled or less, substantially filled—i.e. nearly 99% filled—completely filled, ¼ filled or more, ½ filled or more, or ¾ filled or more. These fractional figures are intended to be examples only, and it is understood that they are not intended to limit this disclosure in any way.

It is understood that embodiments presented herein are meant to be exemplary. Although the present disclosure has been described in detail with reference to certain preferred configurations thereof both in the specification and in the claims, other versions are possible. Embodiments of the present disclosure can comprise any combination of compatible devices/features described herein and/or shown in the figures, and these embodiments should not be limited to those expressly illustrated and discussed. For instance and not by way of limitation, the appended claims could be modified to be multiple dependent claims so as to combine any combinable combination of elements within a claim set, or from differing claim sets. Claims depending on one independent claim could be modified so as to depend from a different independent claim. Therefore, the spirit and scope of the disclosure should not be limited to the versions described above.

While the foregoing written description of the disclosure enables one of ordinary skill to make and use what is considered presently to be the best mode thereof, those of ordinary skill will understand and appreciate the existence of variations, combinations, and equivalents of the specific embodiments, methods, systems, and examples herein. The disclosure should therefore not be limited by the above described embodiments, methods, systems, and examples. Furthermore, certain terminology has been used for the purposes of descriptive clarity, and not to limit the present disclosure. It is therefore intended that the following appended claims include all such alterations, modifications and permutations as fall within the true spirit and scope of the present disclosure. No portion of the disclosure is intended, expressly or implicitly, to be dedicated to the public domain if not set forth in the claims.

I claim:

1. A device for treating brain swelling, said device occupying a device volume, said device comprising:
    a solid comprising:
        a semipermeable membrane; and
        solute particles enclosed in said semipermeable membrane;
    wherein said device is configured such that upon at least partial submersion of said solid in a brain fluid, said solute particles cause an osmotic gradient such that a portion of said brain fluid flows into said solid through said semipermeable membrane.

2. The device of claim 1, wherein said solute particles are part of a solution.

3. The device of claim 2, wherein said solution has an osmolarity greater than or equal to 300 mOsm/L.

4. The device of claim 2, wherein said device has an osmolarity between 600 mOsm/L and 1200 mOsm/L.

5. The device of claim 1, wherein said semipermeable membrane is substantially spherical.

6. The device of claim 1, wherein said semipermeable membrane is substantially cylindrical.

7. The device of claim 1, configured such that upon said portion of said brain fluid flowing into said solid, the device volume increases less than a volume of said portion of said brain fluid flowing into said solid.

8. The device of claim 1, wherein said device is configured for at least partial submersion in brain fluid.

9. The device of claim 8, wherein said solute particles are part of a solution, wherein said brain fluid has a brain fluid concentration of solute particles, and wherein a concentration of said solute particles in said solution is higher than said brain fluid concentration of solute particles.

10. The device of claim 1, wherein upon absorption of said portion of said brain fluid, said device volume increases less than a volume of said portion of said fluid.

11. A method for treating brain swelling, comprising:
    forming an opening in a skull of a patient having a brain, wherein said opening is adjacent to a portion of said brain, said portion having excess fluid; and
    inserting a device into said opening, wherein said device is configured to absorb an absorbed amount of a fluid from said portion of said brain;
    wherein said device comprises:
        a solid comprising:
            a semipermeable membrane; and
            solute particles enclosed in said semipermeable membrane;
        wherein said device is configured such that upon said insertion and at least partial submersion of said solid in said fluid, said solute particles cause an osmotic gradient such that said absorbed amount of said fluid flows into said solid through said semipermeable membrane.

12. The method of claim 1, wherein said portion of said brain is damaged.

13. The method of claim 1, wherein said device has an osmolarity greater than the osmolarity of said fluid.

14. The method of claim 1, wherein said device is configured to, upon absorption of said absorbed amount of said fluid, expand less than the original volume of said absorbed amount of said fluid.

15. The method of claim 1, wherein said device comprises a stent, and further comprising inserting said stent into a blood vessel of said brain.

16. The method of claim 15, wherein said stent comprises a material with an osmolarity greater than the osmolarity of said fluid.

17. The method of claim 15, wherein said stent comprises a biodegradable material.

18. The method of claim 1, wherein absorption of said absorbed amount of fluid from said brain causes an increase in internal pressure of said device.

\* \* \* \* \*